(12) United States Patent
Gill et al.

(10) Patent No.: US 10,308,333 B2
(45) Date of Patent: Jun. 4, 2019

(54) SUBMERSIBLE WARMING DEVICE

(71) Applicant: Board of Regents The University of Texas System, Austin, TX (US)

(72) Inventors: Brijesh S. Gill, Houston, TX (US); Kevin Aroom, Houston, TX (US); Charles Cox, Jr., Houston, TX (US)

(73) Assignee: Board of Regents The University of Texas System, Austin, TX (US)

( * ) Notice: Subject to any disclaimer, the term of this patent is extended or adjusted under 35 U.S.C. 154(b) by 261 days.

(21) Appl. No.: 15/519,110

(22) PCT Filed: Oct. 16, 2015

(86) PCT No.: PCT/US2015/055948
§ 371 (c)(1),
(2) Date: Apr. 13, 2017

(87) PCT Pub. No.: WO2016/061459
PCT Pub. Date: Apr. 21, 2016

(65) Prior Publication Data
US 2017/0225757 A1    Aug. 10, 2017

Related U.S. Application Data

(60) Provisional application No. 62/065,111, filed on Oct. 17, 2014.

(51) Int. Cl.
*B63C 11/28* (2006.01)
*A61F 7/00* (2006.01)

(52) U.S. Cl.
CPC ............ *B63C 11/28* (2013.01); *A61F 7/0085* (2013.01); *A61F 2007/0018* (2013.01)

(58) Field of Classification Search
CPC ......... B63C 11/28; A61F 7/0075; F24V 30/00
USPC ...................................... 126/204, 208, 210
See application file for complete search history.

(56) References Cited

U.S. PATENT DOCUMENTS

| | | | | |
|---|---|---|---|---|
| 4,135,361 A | * | 1/1979 | Eisenhaure | ............. B63C 11/28 126/263.01 |
| 4,195,619 A | * | 4/1980 | Hollen | .................... B63C 11/28 126/204 |
| 4,220,804 A | * | 9/1980 | Nielsen | ................. C07C 201/14 568/4 |

(Continued)

*Primary Examiner* — Gregory L Huson
*Assistant Examiner* — Nikhil P Mashruwala
(74) *Attorney, Agent, or Firm* — Patrick K. Steele (57) ABSTRACT

An embodiment of a submersible warming garment comprises a closed fluid loop including a warming conduit disposed in thermal communication with a chamber containing a catalyst and a cooling conduit disposed within a wearable garment. A pump moves the fluid through the warming conduit, where heat is gained, to the cooling conduit, where heat is surrendered to a human wearing the garment, and back to the pump. An actuated valve on a container of fuel and an actuated valve on a container of oxygen are controlled using a controller to provide a combustible mixture into the chamber where the mixture reacts in the presence of a catalytic member to generate heat and combustion by-products. The combustion by-products, including carbon dioxide and water, are one of adsorbed and absorbed by a carbon dioxide scrubber and a reusable water storage medium. A fan moves the by-products into the scrubber and water storage medium.

20 Claims, 6 Drawing Sheets

(56) References Cited

U.S. PATENT DOCUMENTS

| | | | | |
|---|---|---|---|---|
| 4,294,225 A | * | 10/1981 | Mayo | B63C 11/28 |
| | | | | 126/204 |
| 9,914,512 B2 | * | 3/2018 | Said | B63C 11/04 |
| 2001/0018915 A1 | * | 9/2001 | Nuckols | F23C 13/00 |
| | | | | 126/204 |
| 2007/0093885 A1 | * | 4/2007 | Anderson | A61F 7/00 |
| | | | | 607/104 |

* cited by examiner

SUBMERSIBLE WARMING DEVICE

STATEMENT OF RELATED APPLICATIONS

This application depends from and claims priority to PCT/US2015/055948 entitled Submersible Warming Device filed on Oct. 16, 2015, which depends from and claims priority to U.S. Provisional Application No. 62/065,111 filed on Oct. 17, 2014.

BACKGROUND

Field of the Invention

The present invention relates to a body-warming apparatus for use by a user such as, for example, a diver to maintain body heat during submersion. The portion of the apparatus that provides heat to the user is a heated garment or article worn by or secured to the user. The remaining portion is carried by the user along with other gear.

Background of the Related Art

A diver can remain submerged in water only for as long as he can maintain sufficient body heat to prevent hypothermia. The inability to maintain sufficient body heat can result in shivering, hypertension, tachycardia, tachypnea, vasoconstriction, mental confusion, diuresis and hepatic dysfunction. Severe hypothermia can result in a faltering heart rate, respiratory rate and low blood pressure and even death.

A submerged diver loses heat to the surroundings much more quickly than heat is lost in cold air. A water temperature of 10° C. (50° F.) can result in death in as little as one hour, and can impair motor skills in just minutes without proper maintenance of body heat.

One drawback to the use of conventional body warmers is the production of bubbles. A diver may wish to remain undetectable during a dive, and this is difficult when bubbles are being generated by the diver's equipment and released into the surrounding water. The bubbles migrate to the surface where they can be seen by observers on or at the surface of the water.

Other hostile environments that may require equipment to maintain body heat include environments in which a user is "submerged" in corrosive, poisonous or combustible gas mixtures, or very cold environments that will not tolerate or support an open combustion system. For example, but not by way of limitation, cold gas environs, within a gas storage facility or tank, the vicinity of natural gas or liquefied gas storage or processing tanks or in some areas of a liquefied natural gas tanker. It will be understood that the term "user," as that term is used herein, may refer to a diver or it may refer to a person that is or will be exposed to environmental conditions in which the body's natural ability to regulate the body temperature is insufficient and in need of supplemental heat for personnel safety.

BRIEF SUMMARY

In one embodiment, the present invention provides an apparatus that can provide heat to a submerged diver without releasing bubbles that can be seen by observers at the surface. In one embodiment, the present invention provides an apparatus that can provide heat to a user that is exposed to very cold or hostile environmental conditions.

One embodiment of the system of the present invention comprises an electrically powered fan having an inlet and an outlet, an electrically powered pump having a suction, discharge and a pumping chamber therebetween, one or more batteries to provide electrical current to operate the fan and the pump, a fuel storage container containing a volume of pressurized fuel, a fuel feed valve with an actuator to operate the valve and to control the rate at which a stream of fuel is released, an oxygen storage container containing a volume of pressurized oxygen, an oxygen feed valve with an actuator to operate the valve and to control the rate at which a stream of oxygen is released, a heat exchanger having an interior chamber to receive the stream of fuel and the stream of oxygen, a catalytic member received within the interior chamber of the heat exchanger to promote reaction of the fuel and the oxygen to produce heat and combustion by-products, a warming conduit having an inlet coupled to receive a stream of liquid from the pump discharge, an outlet and a warming portion therebetween disposed in thermal communication with the heat exchanger, at least one combustion by-product storage member disposed to receive a discharge stream of combustion by-products from the interior chamber of the heat exchanger, a cooling conduit disposed outside the chamber and including an inlet, and outlet and a cooling portion therebetween coupled to at least one planar fabric member that is adapted for being secured to a human, a liquid feed conduit coupled at a first end to the outlet of the warming conduit and at a second end to the inlet of the cooling conduit, a liquid return conduit coupled at a first end to the outlet of the cooling conduit and at a second end to the pump suction, and a volume of liquid disposed within a closed loop including the warming conduit, the cooling conduit, the liquid feed conduit, the liquid return conduit, the pump inlet, a pumping chamber intermediate the pump inlet and the pump outlet and within a housing of the pump, and the pump outlet, wherein the pump operates to move liquid through the closed loop, wherein the liquid moving through the warming conduit is warmed by the heat produced in the interior chamber, wherein the liquid moving through the cooling conduit is cooled by the human to whom the planar fabric member is secured, and wherein the combustion by-products are moved by the fan into the combustion by-product storage member where the combustion by-products are absorbed.

In one embodiment of the present invention, the fuel is one of a hydrocarbon and an alcohol. For example, but not by way of limitation, the fuel may be one of methane, ethane, propane, butane, methanol or ethanol. In one embodiment of the present invention, the liquid used in the closed loop is stable and has a low viscosity for low flow resistance. For example, but not by way of limitation, the liquid is one of water, oil, a fluorocarbon and a derivative of a fluorocarbon.

DETAILED DESCRIPTION

Figure 1:
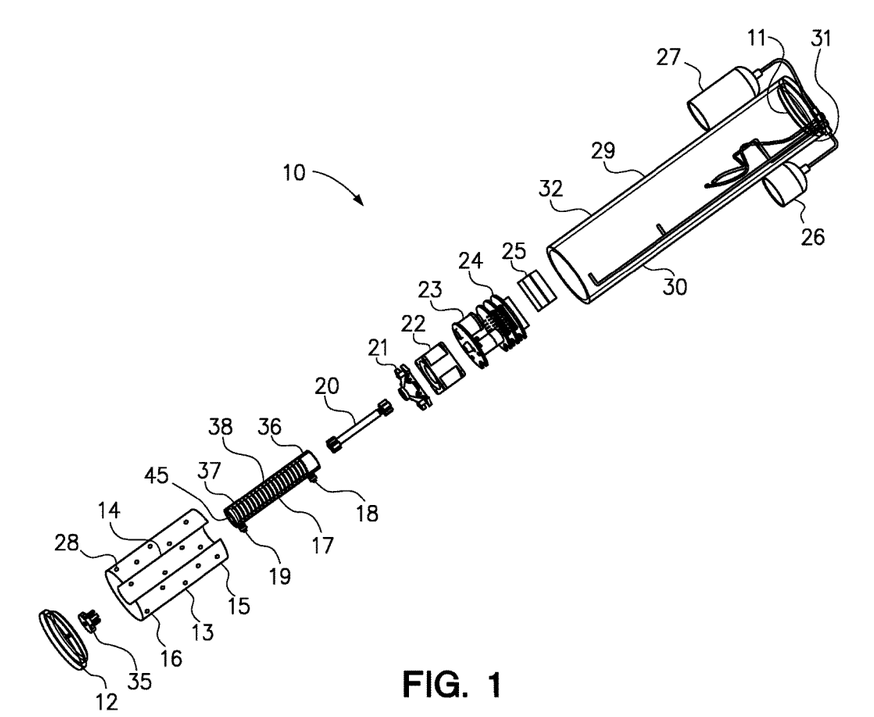
FIG. 1 is an exploded view of an embodiment of a combustion assembly of the apparatus and system of the present invention.

FIG. 1 is an exploded view of an embodiment of a combustion assembly 10 of the apparatus and system of the present invention. The combustion assembly 10 illustrated in FIG. 1 comprises an elongate housing 29 having a proximal end 31, a distal end 32 and an interior space 30 therebetween to receive a plurality of components to be discussed below. The combustible assembly 10 further includes a proximal cap 11 to sealably engage the proximal end 31 of the housing 29 and a distal cap 12 to sealably engage the distal end 32 of the housing 29. At least one of: the housing 29, the proximal cap 11 and the distal cap 12; include one or more sealed conduit ports through which conduits penetrate to supply warmed liquid from within the interior space 30 of the housing 29 to a heat exchanger assembly 50 (see FIG. 3) external to the housing 29 (not shown in FIG. 1—see FIG. 3), and to return cooled liquid from the heat exchanger assembly 50 to within the housing 29. In embodiments such as the one illustrated in FIGS. 1 and 2, additional sealed conduit ports are required for the conduits that deliver fuel and oxygen form the fuel storage container 27 and the oxygen storage container 26.

The combustion assembly 10 of FIG. 1 further comprises a desiccant containing carbon dioxide scrubber 13 having a proximal end 15, a distal end 16 and an interior chamber 14. The desiccant containing carbon dioxide scrubber 13 in FIG. 1 has a cylindrical shape that generally conforms to the interior space 30 of the housing 29. The desiccant pellets 28 are illustrated as being dispersed and suspended within the carbon dioxide scrubber 13. The combustion assembly 10 further comprises a heat exchanger 17 having a proximal end 36, a distal end 37, an interior catalyst chamber 45 (not shown in FIG. 1), and a coiled conduit 38 having an inlet 18 and an outlet 19. The coiled conduit 38 wraps around the heat exchanger 17 between the inlet 18 and the outlet 19 a plurality of times to dispose a substantial length of the coiled conduit 38 in thermally conductive engagement with the heat exchanger 17. The combustion assembly 10 further comprises a catalytic member 20 shaped so to be receivable within the interior catalyst chamber 45 of the heat exchanger 17. The catalytic member 20 provides a large surface area on which a catalyst is disposed for promoting the reaction of the fuel from the fuel storage container 27 with the oxygen from the oxygen storage container 26, as will be described in detail below.

The combustion assembly 10 of FIG. 1 further includes a fuel/air manifold 21, a pump 22, a fan 23, a controller 24, one or more batteries 25, a fuel storage container 27 and an oxygen storage container 26. It will be noted that the fuel storage container 27 is proximal to the proximal end 31 of the housing 29 and the catalytic member 20 is disposed within the catalyst chamber 45 of the heat exchanger 17, which is proximal to the distal end 32 of the housing 29 to prevent unwanted heating of the fuel storage container 27 by the combustion within the catalyst chamber 45.

Figure 2:
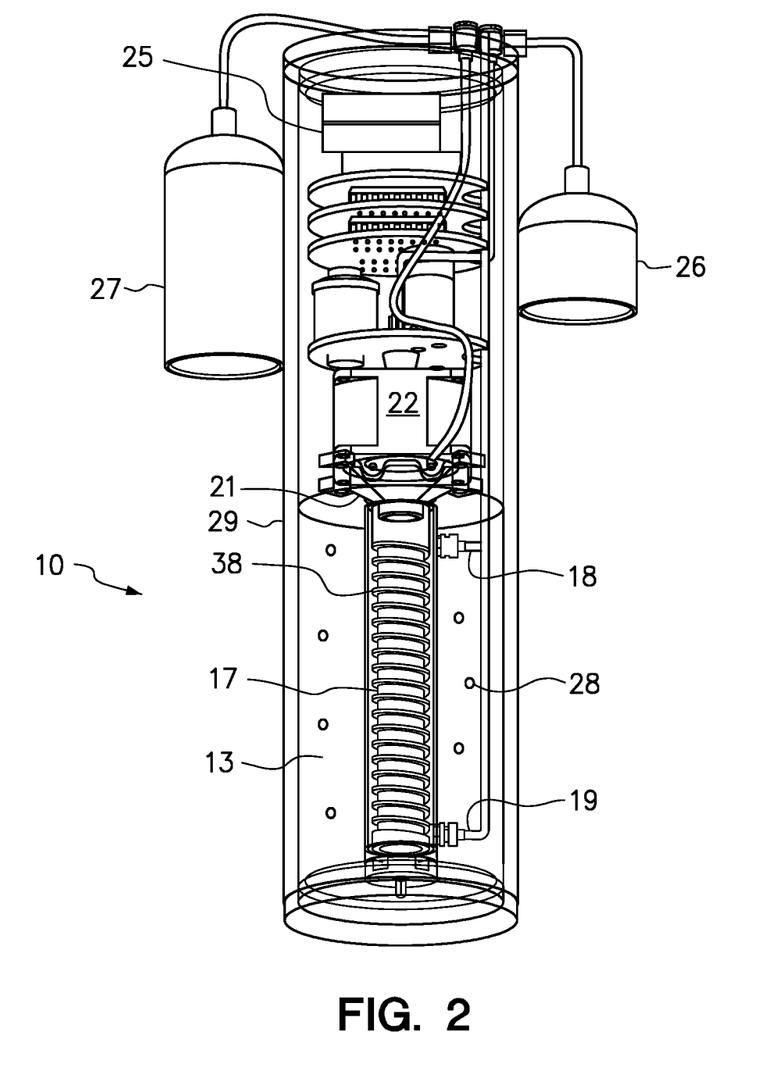
FIG. 2 is the assembled combustion assembly of FIG. 1.

FIG. 2 is the assembled combustion assembly 10 of FIG. 1 illustrating how many of the water-sensitive components shown in the exploded view of FIG. 1 can be arranged within the interior space 30 of the housing 29. The assembled combustion assembly 10 of FIG. 2 includes the oxygen storage container 26 and the fuel storage container 27, both of which are illustrated as being external to the housing 29, the heat exchanger 17 with the coiled conduit 38 thereon, the desiccant containing carbon dioxide scrubber 13, the fuel/air manifold 21, the fan 23 and the pump 22. It will be understood that the oxygen storage container 26 and the fuel storage container 27 can be included among the components disposed within the interior space 30 of a larger housing 29 or within the same housing if other components are made smaller.

Figure 3:
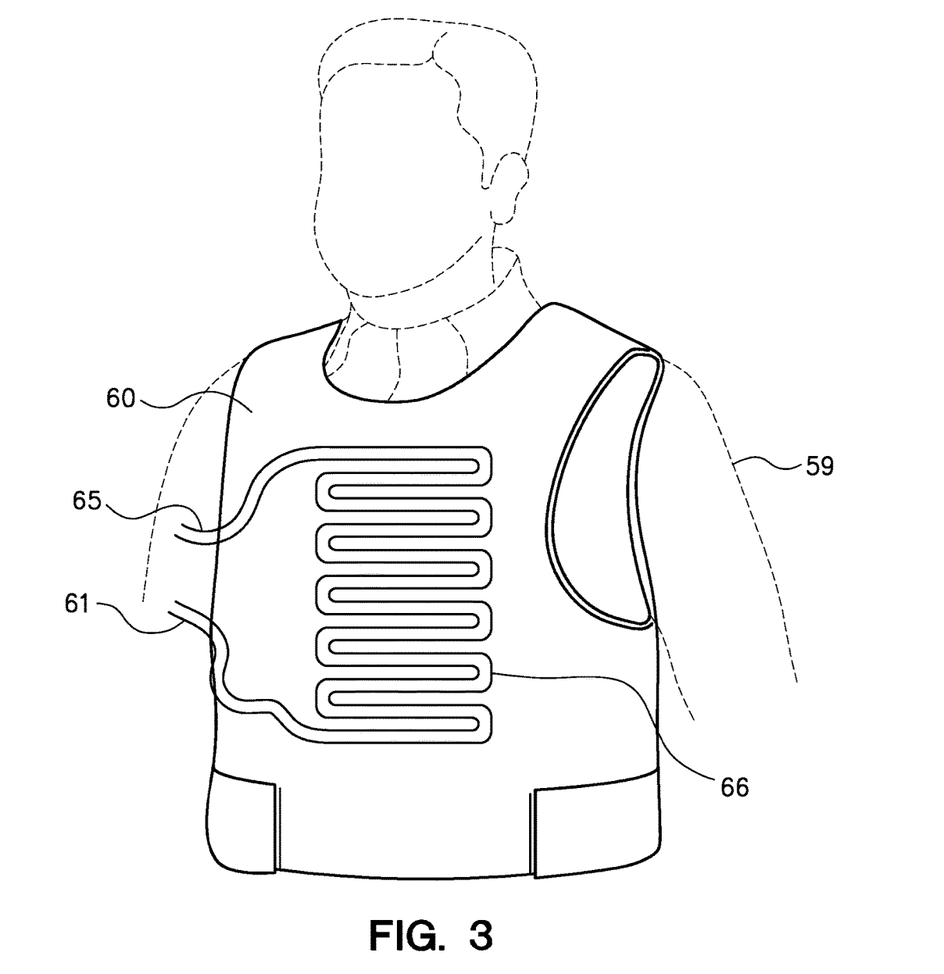
FIG. 3 is a perspective view of an embodiment of a heat exchanger assembly wearable by a user and compatible with the combustion assembly of FIGS. 1 and 2.

FIG. 3 is a perspective view of an embodiment of a heat exchanger assembly 50 wearable by a user 59 and compatible for use by the user 59 along with the combustion assembly 10 illustrated in FIGS. 1 and 2. The heat exchanger assembly 50 includes a garment 60, which in FIG. 3 is a vest, to which a cooling conduit 66 is secured in a serpentine or "switchbacked" pattern to provide for a greater length over which heat transfer to the user 59 can occur. The cooling conduit 66 includes a warmed liquid feed conduit 61 and a cooled liquid return conduit 65.

Figure 4:
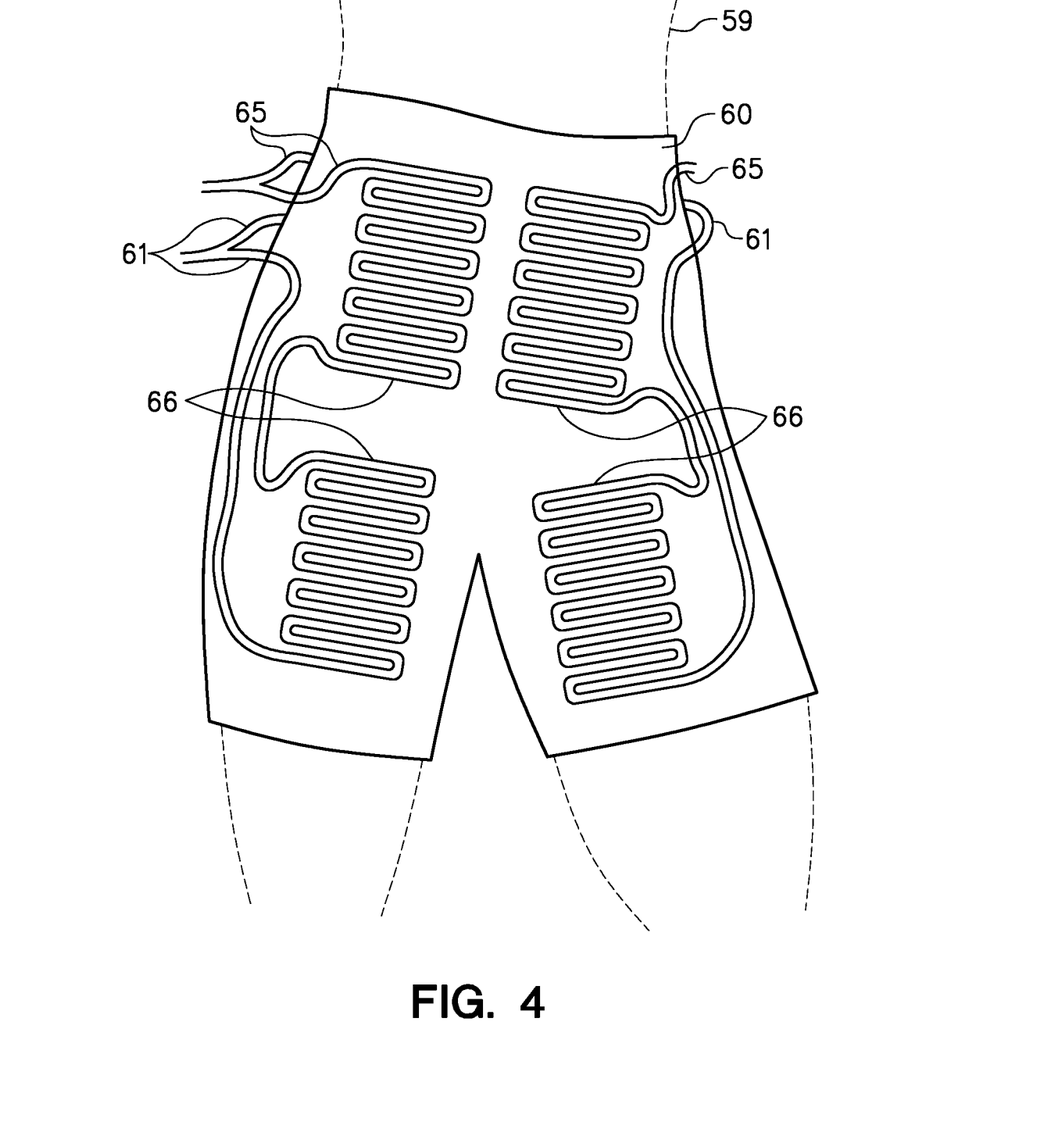
FIG. 4 is a perspective view of an embodiment of a heat exchanger assembly wearable by a user and compatible with the combustion assembly of FIGS. 1 and 2.

FIG. 4 is a perspective view of another embodiment of a heat exchanger assembly 50 wearable by a user 59 and compatible for use by the user 59 along with the combustion assembly 10 illustrated in FIGS. 1 and 2. The heat exchanger assembly 50 includes a garment 60, which in FIG. 4 is a pair of trousers or shorts, to which a cooling conduit 66 is secured in a serpentine or "switchbacked" pattern similar to that illustrated in FIG. 3 to provide for a greater length over which heat transfer to the user 59 can occur. The cooling conduit 66 includes a warmed liquid feed conduit 61 and a cooled liquid return conduit 65. It will be understood that the garment 60 of FIG. 4 is an example only and, in other embodiments, the garment 60 may include extended leg portions with extended conduits 66 to carry warmed coolant to the user's lower legs. FIG. 4 also illustrates how a plurality of cooling conduits 66 can be fluidically coupled in parallel and/or in series to distribute warmed coolant to separated body parts.

Figure 5:
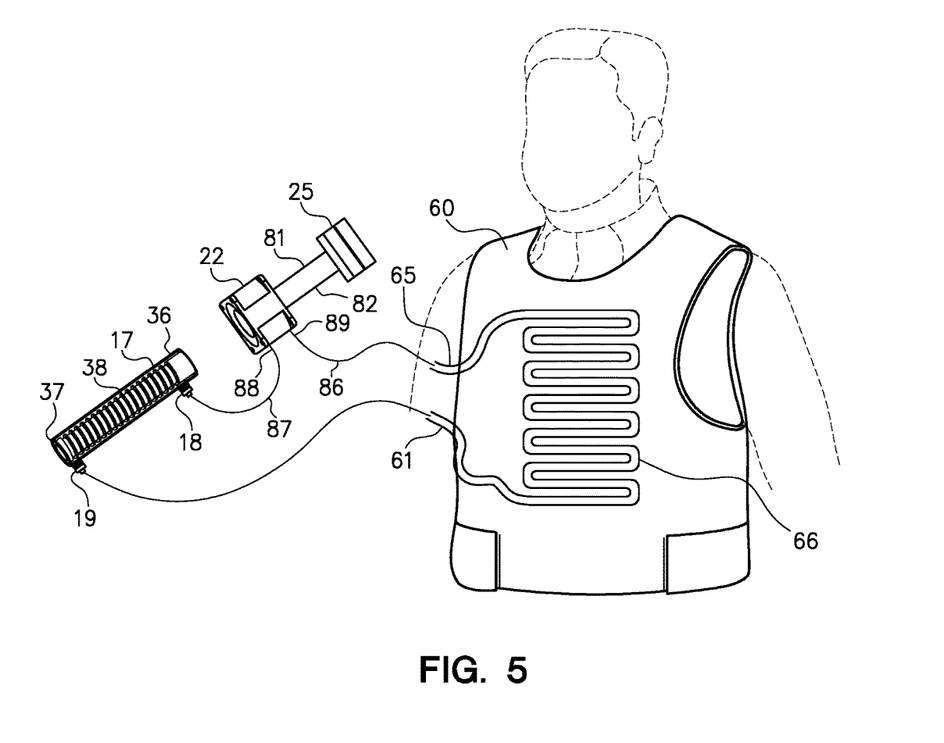
FIG. 5 is an illustration of the components of an embodiment of the present invention that make up a closed liquid loop of the apparatus and system of the present invention.

FIG. 5 is an illustration of the components of an embodiment of the present invention that make up a closed fluid loop of the apparatus and system of the present invention. The closed fluid loop includes the coiled conduit 38 that is wrapped around the heat exchanger 17 between the proximal end 36 and the distal end 37 of the heat exchanger 17. The coiled conduit 38 includes an inlet 18 to receive cooled liquid from the discharge outlet 88 of the pump 22 and an outlet 19 from which warmed liquid flows into the warmed liquid feed conduit 61 to the cooling conduit 66 that is secured to the garment 60 worn by the user 59. The cooling conduit 66 within the fabric of the warming garment 60 terminates at the cooled liquid return conduit 65 through which liquid cooled in the garment 60 flows to the suction inlet 89 of the pump 22. The pump 22 is a motorized pump that includes an electric motor that is powered by battery 25 through conductive conduits (wires) 81 and 82. It will be understood that the closed liquid loop of FIGS. 4 and 5 may, in some embodiments, include insulation to reduce heat loss in the warmed liquid feed conduit 61 or the cooled liquid return conduit 65, in addition to check valves to manage fluid flow and bleed valves for use in removing unwanted air bubbles from the closed loop.

Figure 6:
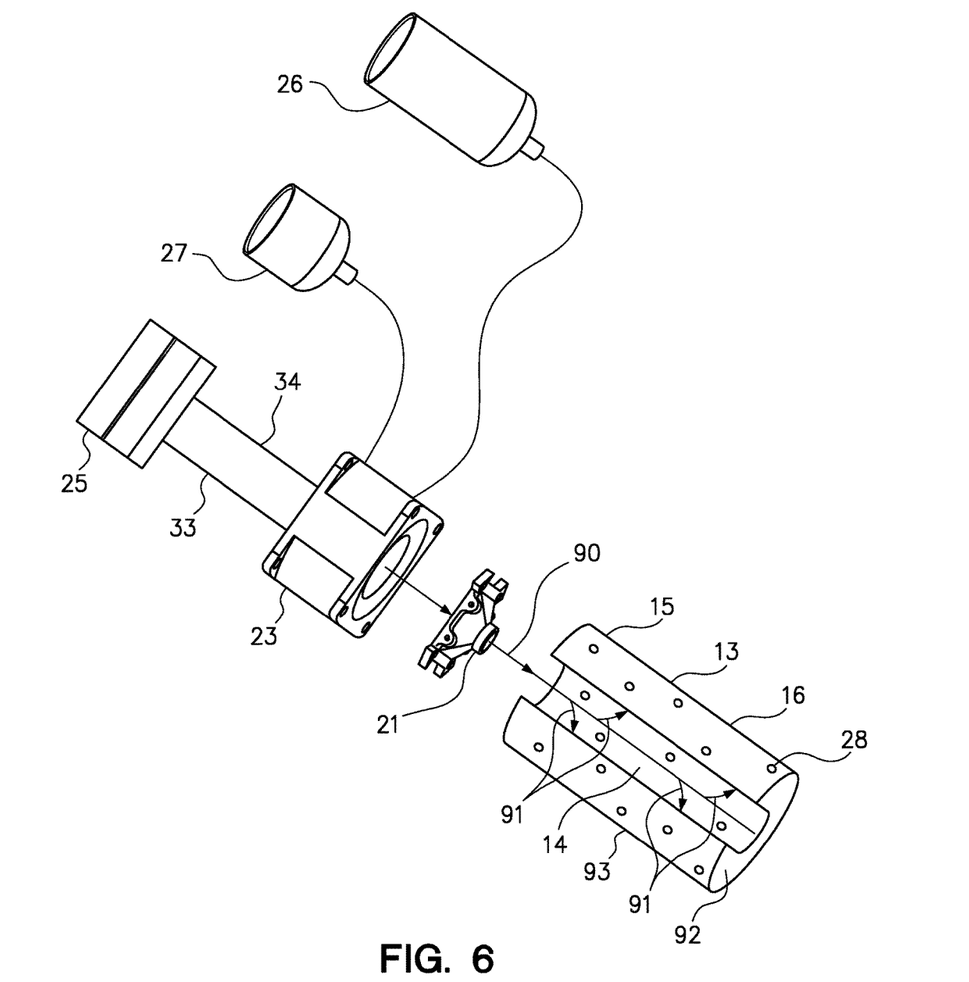
FIG. 6 is an illustration of the components of an embodiment of the present invention that together store the reactants and the combustion by-products, and that generate heat.

FIG. 6 is an illustration of the components of an embodiment of the present invention that together store the reactants and the combustion by-products, and that generate heat. FIG. 6 illustrates the use of the battery 25 to provide current flow through conductive conduits (wires) 92 and 93 to a motorized fan 23 that receives a stream of fuel released from fuel storage container 27 and a stream of oxygen released from oxygen storage container 26. The fan 23 serves to mix the streams of fuel and oxygen into a combustible mixture, and to pressurize the combustible mixture for feeding the combustible mixture through the fuel/air manifold 21 into a proximal end 15 of an interior chamber 14 of the carbon dioxide scrubber 13 where the combustive mixture reacts in the presence of the catalytic member 20 (not shown in FIG. 6—see FIG. 1) to produce heat and combustion by-products. At least some of the heat generated by the exothermic reaction of the fuel/air mixture transfers through the heat exchanger 17 (not shown—see FIG. 1) to the coiled conduit 38 (not shown—see FIG. 5). The combustion by-products, mainly carbon dioxide and water vapor, emerge from the distal end 16 of the carbon dioxide scrubber 13 and are forced by the presence of the distal cap 12 (not shown—see FIG. 1) adjacent to the distal end 16 of the carbon dioxide scrubber 13 and by the pressure of the fan 23 to enter the distal end 16 of the desiccant containing carbon dioxide scrubber 13 as indicated by arrows 91.

It will be understood that, in the embodiment of the apparatus and system in FIGS. 1-6, that the distal end 16 of the cylindrically-shaped and desiccant containing carbon dioxide scrubber 13 is circular in shape and has a hole in the center at the interior chamber 14. The carbon dioxide in the combustion by-product stream is absorbed by the material of the carbon dioxide scrubber 13 and the water vapor in the combustion by-product stream is absorbed by desiccant pellets dispersed in and supported within the carbon dioxide scrubber 13. Any remaining, unabsorbed combustion by-product 91 exiting the distal end 16 of the desiccant containing carbon dioxide scrubber 13 will be absorbed by the distal face 92 of the desiccant containing carbon dioxide scrubber 13. It will be understood that any remaining, unabsorbed combustion by-product 91 that is not absorbed by the distal face 92 will be diverted by the distal cap 12 of the housing 29 (see FIG. 1) to the annular space intermediate the exterior 93 of the carbon dioxide scrubber 13 for further absorption into the desiccant containing carbon dioxide scrubber 13.

The desiccant containing carbon dioxide scrubber 13 and the desiccant pellets therein, if any, have a limited capacity to absorb carbon dioxide, and that the fuel storage container 27 and the oxygen storage container 26 each have a limited capacity to store fuel and oxygen, respectively. It will be understood that the volume of carbon dioxide produced can be correlated to the amount of fuel required to produce that volume of carbon dioxide, and that the amount of oxygen to combust the amount of fuel can also be determined. The anticipated duration of the dive and the anticipated temperature of the water are critical to determining how much fuel will be required to provide heat to the user 59 for that duration. Even the service time for the battery to power the pump 22 and fan 23 can be determined in advance of use of the apparatus and system of the present invention.

It will be understood that the desiccant pellets may be separated from the carbon dioxide scrubber 13 in some embodiments of the apparatus of the present invention, and that the disclosure of a carbon dioxide scrubber 13 having a plurality of desiccant pellets distributed within and supported by the carbon dioxide scrubber 13 is a matter of convenience and practicality because the combustion by-products include a mixture of carbon dioxide and water vapor. The desiccant pellets of the carbon dioxide scrubber 13 of embodiments of the present invention may comprise one or more of silica, activated charcoal, calcium sulfate, calcium chloride and molecular sieves.

Preferably, in one or more alternate embodiments, the apparatus and system of the present invention includes one or more of a hydrocarbon sensor, an oxygen sensor, a humidity sensor, a temperature sensor and a pressure sensor. These sensors may be used in conjunction with a controller to monitor and control the combustion process.

For example, but not by way of limitation, a hydrocarbon sensor may be disposed upstream of the carbon dioxide scrubber to sense the concentration of unburned hydrocarbon gas, if any, entering the carbon dioxide scrubber. Unburned hydrocarbon gas would indicate that the combustible mixture of oxygen and fuel is too "rich," meaning too much fuel for the rate at which oxygen is introduced into the combustion process.

As another example, an oxygen sensor might be deployed to sense the amount of oxygen entering the carbon dioxide scrubber. An excessive amount of oxygen entering the carbon dioxide scrubber would indicate that the combustible mixture may be running too "lean," meaning an insufficient rate of fuel for the rate at which oxygen is introduced into the combustion process.

As another example, a humidity sensor might be deployed to sense the humidity in the combustion by-product stream entering the carbon dioxide scrubber. The humidity sensor will detect dramatic increases in the humidity level within the housing that contains the components of the device. An increasing humidity level will indicate either saturation of desiccant pellets or failure of the water absorption system.

A temperature sensor may be deployed to sense the temperature of the fluid being discharged from the combustion assembly to the external heat exchanger assembly secured to the diver. An excessive temperature of the fluid would indicate that fuel and oxygen are being unnecessarily wasted and that the heat exchanger assembly secured to the diver is being maintained at an excessive temperature for the conditions. An insufficient temperature of the fluid would indicate that the rate of fuel and/or oxygen entering the combustion process is insufficient for the conditions. In one embodiment of the apparatus and system of the present invention, an additional temperature sensor is provided to monitor the temperature within the catalyst chamber. For example, a low catalyst chamber temperature, near ambient, would serve as an indicator that the apparatus and system are inactive and in a condition suitable for start-up. As another example, a high catalyst chamber temperature would serve as an indicator that there is a restriction in the closed fluid loop that prevents the heat exchanger from being continuously cooled. In one embodiment of the apparatus and system of the present invention, the temperature sensor may be a 10 k NTC thermistors to sense (measure) fluid temperature. NTC thermistors are available from AVX, EPCOS, GE, Honeywell, Murata, Vishay and other sources.

A pressure sensor may be deployed to sense the pressure of the fluid stream being delivered from the combustion assembly to the external heat exchanger that is secured to the diver. An excessive pressure would indicate either that the pump is being operated at an excessive speed or that there is a restriction in the heat exchanger conduit in the heat exchanger assembly secured to the diver. An insufficient pressure would indicate that the pump is being operated at an insufficient speed or that there is a leak in the closed loop. Additional pressure sensors may be used to monitor the pressure within the fuel storage container and the pressure within the oxygen storage container. Another pressure sensor may be used to monitor the catalyst chamber to provide an alert or to close one or both of the fuel valve and the oxygen valve in the event of an overpressurization event.

A battery sensor may be deployed to monitor the power level of the battery and to alert the user in the event that the battery power level falls below a predetermined alert level. It will be understood that a loss in battery power would render the fuel valve actuator and the oxygen valve actuator, in addition to the pump and the fan, inoperable.

In one embodiment of the apparatus and system of the present invention, the carbon dioxide scrubber comprises Sodasorb® carbon dioxide absorbent or some other absorbent that selectively absorbs gaseous carbon dioxide from the stream of combustion by-products emerging from the catalyst housing. The carbon dioxide scrubber may contain a chemical that changes color when depleted or nearly depleted to provide a visual alert or a visual confirmation of the dwindling capacity of the carbon dioxide scrubber. In another embodiment of the apparatus and system of the present invention, the carbon dioxide scrubber comprises a Sofnolime® product such as, for example, Sofnolime® 797 or Sofnolime® CD. Sofnolime® is a product available from Molecular Products, Inc. of Boulder, Colo., USA. Embodiments of the carbon dioxide scrubber may further comprise desiccator pellets mixed into the carbon dioxide absorbent or confined to a separate compartment in the carbon dioxide scrubber from the carbon dioxide absorbent. The desiccator pellets will absorb the moisture component of the combustion by-products.

The fan is needed to provide a positive head to move the reactants (fuel and oxygen) into the catalyst compartment of the heat exchanger and to move the combustion by-products from the catalyst chamber into the carbon dioxide scrubber, which includes the desiccant pellets. The fan is electrically powered using the one or more batteries. It will be understood that the fan capacity should be selected to minimize power consumption and to provide sufficient head to move the anticipated rate of combustion by-products through the carbon dioxide scrubber.

In one embodiment of the apparatus and system of the present invention, the discharge outlet from the oxygen valve and/or the discharge outlet from the fuel valve are positioned immediately upstream of the fan to promote mixing of the fuel and the oxygen before the combustible stream enters the catalyst chamber.

In one embodiment of the apparatus and system of the present invention, the housing is sealed to prevent water intrusion into the housing 29. It will be understood that water, were it to contact the carbon dioxide scrubber 13, the desiccant pellets therein, the catalyst member 20 or the controller and the various sensors, would cause failure or diminished performance of these components. The use of a proximal cap 11 and distal cap 12 enables the sealing of the proximal end 31 and the distal end 32 of the housing 29 to prevent water intrusion. The sealed housing 29 gives rise to the potential for over-pressurization of the housing 29. In one embodiment of the apparatus and system of the present invention, a passive pressure relief device such as, for example, a spring-biased safety relief valve and/or a rupture disc, may be included within the housing 29, the proximal cap 11 or the distal cap 12 to protect against housing rupture due to internal over-pressurization.

It will be understood that, in some embodiments, the rate at which fuel is released from the fuel storage container 27 can be controlled by a fuel valve and the fuel valve actuator. Similarly, the rate at which oxygen is released from the oxygen storage container 26 can be controlled by the oxygen valve and the oxygen valve actuator. In addition, a manual shut-off valve on the fuel storage container 27 and a manual shut-off valve on the oxygen storage container 26 will facilitate safer assembly and operation of embodiments of the apparatus and system of the present invention.

The shape and weight distribution of the combustion assembly of the apparatus and system of the present invention may be adapted for conveniently being secured to a user 59. For example, but not by way of limitation, a vertical "stack" arrangement enables the combustion assembly to be secured to the back of a user with the proximal end 31 disposed upwardly, or proximal to the user's 59 head, and the distal end 32 to be disposed downwardly, or proximal to the user's 59 lower abdomen. This arrangement is frequently used by SCUBA divers for a breathing tank or by personnel entering a hostile environment for a respirator, air supply or air filtration unit.

In one embodiment of the apparatus and system of the present invention, a purge valve penetrating a wall of the housing 29 is provided to enable the housing 29 to be purged using, for example, an inert gas, to remove any free hydrocarbons from the housing 29 prior to start-up and use.

It will be understood that the various signals generated by one or more hydrocarbon sensors, oxygen sensors, humidity sensors, pressure sensors and/or temperature sensors will be routed to a controller, and that the controller would be programmed to generate output signals to the pump 22 to control the pump 22 speed, the fan 23 to control the fan 23 speed, the fuel valve actuator to control the rate at which fuel is released into the combustion process, and the oxygen valve actuator to control the rate at which oxygen is released into the combustion process. A microprocessor unit (MPU) having sufficient ports for sensor signal inputs and control signal outputs will perform this function. A model no. 8051f330 chip from Silicon Labs, Inc. or from other sources would be useful for many applications.

The foregoing embodiments that include a microprocessor for control of valves, fan speed, pump speed or other components may include computer readable program code for implementing or initiating any one or more aspects of the methods described herein. Accordingly, a separate description of the methods will not be duplicated in the context of a computer program product.

As will be appreciated by one skilled in the art, aspects of the present invention that include an MPU may be controlled or monitored using one or more computer program product codes. Accordingly, some automated or highly-controlled aspects of the present invention may take the form of an entirely hardware embodiment or an embodiment combining software and hardware aspects.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, components and/or groups, but do not preclude the presence or addition of one or more other features, integers, steps, operations, elements, components, and/or groups thereof. The terms "preferably," "preferred," "prefer," "optionally," "may," and similar terms are used to indicate that an item, condition or step being referred to is an optional (not required) feature of the invention.

The corresponding structures, materials, acts, and equivalents of all means or steps plus function elements in the claims below are intended to include any structure, material, or act for performing the function in combination with other claimed elements as specifically claimed. The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A submersible warming device, comprising:
an electrically powered fan having an inlet and an outlet;
an electrically powered pump having a suction, discharge and a pumping chamber therebetween;
one or more batteries to provide electrical current to operate the fan and the pump;
a fuel storage container containing a volume of pressurized fuel;
a fuel feed valve with an actuator to operate the valve and to control the rate at which a stream of fuel is released;
an oxygen storage container containing a volume of pressurized oxygen;
an oxygen feed valve with an actuator to operate the valve and to control the rate at which a stream of oxygen is released;
a heat exchanger having an interior chamber to receive the stream of fuel and the stream of oxygen;
a catalytic member received within the chamber of the heat exchanger to promote reaction of the fuel and the oxygen to produce heat and reaction by-products;
a warming conduit having an inlet coupled to the pump discharge, an outlet and a warming portion therebetween disposed in thermal communication with the heat exchanger;
at least one combustion by-product storage member disposed to receive a discharge stream of combustion by-product gases from the interior chamber of the heat exchanger;
a cooling conduit including an inlet, and outlet and a cooling portion therebetween coupled to at least one planar fabric member that is adapted for being secured to a human;
a fluid feed conduit coupled at a first end to the outlet of the warming conduit and at a second end to the inlet of the cooling conduit;
a fluid return conduit coupled at a first end to the outlet of the cooling conduit and at a second end to the pump suction; and
a volume of fluid disposed within a closed loop including the warming conduit, the cooling conduit, the fluid feed conduit, the fluid return conduit, the pump inlet, the pump outlet, and a pumping chamber intermediate the pump inlet and the pump outlet.

2. The submersible warming device of claim 1, further comprising a housing;
wherein the battery, the fuel storage container, the oxygen storage container, the cylindrical heat exchanger, the warming conduit, and the combustion by-products storage member are together contained within the housing.

3. The submersible warming device of claim 2, wherein the housing is elongate and cylindrical.

4. The submersible warming device of claim 1, wherein the combustion by-products storage member includes a desiccant.

5. The submersible warming device of claim 1, wherein the combustion by-products storage member includes a carbon dioxide absorbing material.

6. The submersible warming device of claim 5, wherein the combustion by-products storage member includes one of a zeolite, an amine, an oxide and a hydroxide.

7. The submersible warming device of claim 6, wherein the combustion by-products storage member further includes a desiccant.

8. The submersible warming device of claim 1, wherein the warming conduit includes a plurality of coils disposed around the chamber to increase a length of the warming conduit over which heat transfer from the chamber to the warming conduit occurs.

9. The submersible warming device of claim 2, wherein the housing is insulated and sealed to prevent water intrusion into the housing interior upon submersion of the submersible warming device in water.

10. The submersible warming device of claim 2, further comprising a controller to control at least one of the fuel valve actuator, the oxygen valve actuator, current from the one or more batteries to the fan, current from the one or more batteries to the pump.

11. The submersible warming device of claim 7, wherein the desiccant comprises one of silica, activated charcoal, calcium sulfate, calcium chloride and a molecular sieve material.

12. The submersible warming device of claim 1, wherein the warming fluid comprises one of water and an oil.

13. The submersible warming device of claim 1, further comprising a temperature sensor disposed in thermal communication with one of the fluid feed conduit and the fluid return conduit.

14. The submersible warming device of claim 13, wherein the temperature sensor generates a signal to a controller that controls the fuel valve actuator and the oxygen valve actuator.

15. The submersible warming device of claim 1, wherein the planar fabric member is a portion of a garment worn by the human to deter hypothermia.

16. The submersible warming device of claim 15, wherein the cooling portion of the cooling conduit includes a serpentine pathway having a plurality of switchbacks.

17. The submersible warming device of claim 1, wherein the pump operates to move fluid through the closed loop.

18. The submersible warming device of claim 1, wherein the fluid moving through the warming conduit is warmed as a result of heat transferred from the heat exchanger.

19. The submersible warming device of claim 1, wherein the fluid moving through the cooling conduit is cooled as a result of heat transfer from the cooling conduit to the human to whom the planar fabric member is secured.

20. The submersible warming device of claim 1, wherein the combustion by-products are moved by the fan into the combustion by-product storage member where the combustion by-products are absorbed.

* * * * *

UNITED STATES PATENT AND TRADEMARK OFFICE
CERTIFICATE OF CORRECTION

| | | |
|---|---|---|
| PATENT NO. | : 10,308,333 B2 | Page 1 of 1 |
| APPLICATION NO. | : 15/519110 | |
| DATED | : June 4, 2019 | |
| INVENTOR(S) | : Brijesh S. Gill, Kevin Aroom and Charles Cox, Jr. | |

It is certified that error appears in the above-identified patent and that said Letters Patent is hereby corrected as shown below:

In the Specification

Column 1 Line 2 Insert under the heading:
--GOVERNMENT SUPPORT CLAUSE
The invention was made with government support under Grant No. W81XWH-04-1-0729 awarded by the U.S. Department of Defense. The government has certain rights in the invention.--

Signed and Sealed this
Tenth Day of September, 2019

Andrei Iancu
*Director of the United States Patent and Trademark Office*

UNITED STATES PATENT AND TRADEMARK OFFICE
CERTIFICATE OF CORRECTION

| | |
|---|---|
| PATENT NO. | : 10,308,333 B2 |
| APPLICATION NO. | : 15/519110 |
| DATED | : June 4, 2019 |
| INVENTOR(S) | : Brijesh S. Gill, Kevin Aroom and Charles Cox, Jr. |

It is certified that error appears in the above-identified patent and that said Letters Patent is hereby corrected as shown below:

In the Specification

Please insert, in Column 1, after the portion entitled STATEMENT OF RELATED APPLICATIONS and before the portion entitled BACKGROUND, the following Government Support Clause:
--This invention was made with government support under W81XWH-04-1-0729 awarded by the Department of Defense. The government has certain rights in the invention.--

This certificate supersedes the Certificate of Correction issued September 10, 2019.

Signed and Sealed this
Sixteenth Day of May, 2023

Katherine Kelly Vidal
*Director of the United States Patent and Trademark Office*